US012752067B2

(12) United States Patent
Van Den Ende et al.

(10) Patent No.: US 12,752,067 B2
(45) Date of Patent: Oct. 6, 2026

(54) AUTO IDENTIFICATION OF PATIENT INTERFACE BASED ON CHANGES IN A PRESSURE SUPPORT SYSTEM

(71) Applicant: KONINKLIJKE PHILIPS N.V., Eindhoven (NL)

(72) Inventors: Daan Anton Van Den Ende, Breda (NL); Joyce Van Zanten, Waalre (NL); Jonathan Sayer Grashow, Cheswick, PA (US); Joachim Johannes Kahlert, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 463 days.

(21) Appl. No.: 18/544,559

(22) Filed: Dec. 19, 2023

(65) Prior Publication Data

US 2024/0207551 A1 Jun. 27, 2024

Related U.S. Application Data

(60) Provisional application No. 63/434,491, filed on Dec. 22, 2022.

(51) Int. Cl.
*A61M 16/00* (2006.01)
*A61M 16/06* (2006.01)

(52) U.S. Cl.
CPC ...... *A61M 16/024* (2017.08); *A61M 16/0066* (2013.01); *A61M 16/0683* (2013.01);
(Continued)

(58) Field of Classification Search
CPC .... A61M 16/00–0003; A61M 16/0051; A61M 16/0057–0069;
(Continued)

(56) References Cited

U.S. PATENT DOCUMENTS

| | | | |
|---|---|---|---|
| 7,191,780 | B2 | 3/2007 | Faram |
| 8,695,602 | B2 | 4/2014 | Pierro |

(Continued)

FOREIGN PATENT DOCUMENTS

| | | | |
|---|---|---|---|
| DE | 102015003953 | A1 | 10/2015 |

OTHER PUBLICATIONS

Zhu X. et al., "Assessment of the Performance of Nasal Pillows at High CPAP Pressures", Journal of Clinical Sleep Medicine, vol. 9, No. 9, pp. 873-877, Sep. 2013.

Merilampi S. et al., "Printed Passive UHF RFID Tags as Wearable Strain Sensors", 2010 3rd International Symposium on Applied Sciences in Biomedical and Communication Technologies (ISABEL 2010), pp. 1-5, 2010.

Mcgee K. et al., "Proof of Concept Novel Configurable Chipless RFID Strain Sensor", Sensors 2021, 21(18), 6224, 2021.

*Primary Examiner* — Rachel T Sippel
(74) *Attorney, Agent, or Firm* — Michael W. Haas

(57) ABSTRACT

A system and method of identifying a patient interface device change in a pressure support system having a controller based on a mask and a headgear worn by a user. A set of force sensors and strap distance sensors are associated with the mask and the headgear such that a controller is able to assess current operational parameters of the mask and headgear. The controller further determines if there is a difference in the current operational parameters when compared to prestored operational parameters. The controller then assesses whether or not the determined change in the operational parameters indicates that the mask worn by the user has been changed.

22 Claims, 9 Drawing Sheets

(52) U.S. Cl.
CPC ............... *A61M 2205/3327* (2013.01); *A61M 2205/6018* (2013.01)

(58) Field of Classification Search
CPC ......... A61M 16/021–024; A61M 16/06–0605; A61M 16/0683; A61M 16/08; A61M 16/0816; A61M 16/0875; A61M 2016/0027; A61M 2205/18; A61M 2205/33; A61M 2205/3306; A61M 2205/3317–332; A61M 2205/3327–3334; A61M 2205/50; A61M 2205/52; A61M 2205/60–6018; A61M 2205/6054–6063; A62B 7/00–02; A62B 7/12; A62B 9/00; A62B 9/006; A62B 9/04; A62B 18/00; A62B 18/006–025; A62B 18/08; A62B 18/084
See application file for complete search history.

(56) References Cited

U.S. PATENT DOCUMENTS

| | | | | |
|---|---|---|---|---|
| 8,766,790 | B2 | 7/2014 | Jacob | |
| 10,124,141 | B2 | 11/2018 | Somervell | |
| 10,279,134 | B2 | 5/2019 | Kwok | |
| 2010/0078019 | A1 * | 4/2010 | Rittner | A62B 9/00 128/204.21 |
| 2013/0118500 | A1 * | 5/2013 | Stevens | A61M 16/024 128/205.25 |
| 2016/0321420 | A1 | 11/2016 | Klee | |
| 2016/0354571 | A1 | 12/2016 | Grashow | |
| 2017/0266400 | A1 * | 9/2017 | McCarthy | A61M 16/06 |
| 2017/0361045 | A1 | 12/2017 | Fu | |
| 2020/0046289 | A1 | 2/2020 | Armitstead | |
| 2021/0069441 | A1 | 3/2021 | Mashal | |

* cited by examiner

AUTO IDENTIFICATION OF PATIENT INTERFACE BASED ON CHANGES IN A PRESSURE SUPPORT SYSTEM

CROSS-REFERENCE TO RELATED APPLICATIONS

This patent application claims the priority benefit under 35 U.S.C. § 119(e) of U.S. Provisional Application No. 63/434,491, filed on Dec. 22, 2022, the contents of which are herein incorporated by reference.

BACKGROUND OF THE INVENTION

1. Field of the Invention

The disclosed concept relates generally to pressure support systems, and, in particular, to a system and method for identifying and alerting users of detected changes in patient interface devices based on the output of a number of sensors coupled to or embodied in the patient interface device so that appropriate changes to therapy settings can be made.

2. BACKGROUND OF THE INVENTION

Today, the first line therapy for patients diagnosed with obstructive sleep apnea syndrome (OSAS) after a sleep test is a pressure assisted ventilation support, most often by continuous positive airway pressure (CPAP) therapy. In moderate and severe patients with an AHI>15, the therapy is reimbursed. In mild OSA patients with daytime symptoms, or with chronic and persistent cardiac comorbidities, the PAP therapy is reimbursed for an AHI>5. Reimbursement covers the PAP device as well as periodic resupply of consumable items, such as tubing, headgear, masks, and cushions. Depending on geography different time periods for replacement of these consumable items are in effect, mostly ranging from 1 month to 6 months.

The proper setup of the PAP device including, for instance, pressure settings and fitting of the mask is done by a qualified sleep clinician, most often in an overnight setting at a sleep lab. However, home titration is a possible alternative for certain patients.

Once the correct machine settings and appropriate consumable items are established, the equipment is supplied by a durable medical equipment (DME) supplier and the patient commences therapy. In the event of difficulties with any aspects of the therapy, a consult, optionally followed by re-titration may be performed, which may result in a change in mask type. For instance, a patient may switch from a nasal mask to an oronasal or full-face mask. This change has to be communicated with the DME, who then provides the new mask to the patient. In addition, patients may also buy a mask out-of-pocket. For instance, if the mask is lost or broken in between reimbursement periods, or if the patient believes that they need a different mask than was advised by the clinician. In either of these cases, the patient may end up using a different mask than was specified by the clinician for their therapy, potentially causing a mismatch in the mask that is used compared to the specified mask. This mismatch potentially has great influence on the therapy because the PAP machine settings are no longer matching the mask being used by the patient.

SUMMARY OF THE INVENTION

These needs, and others, are met by a method of identifying a patient interface device change in a pressure support system having a controller based on a mask and a headgear worn by a user. Further, a number of force sensors and/or a number of strap distance sensors may be associated with the mask and the headgear. The method may include the steps of (a) determining in the controller, while the mask and headgear are worn by the user and are coupled to the pressure support system during operation of the pressure support system, one or more of the following: (i) a total number of leads associated with the number of force sensors, (ii) a strapping force for the mask and headgear based on outputs from the number of force sensors, (iii) a strapping force distribution for the mask and headgear based on the outputs from at least one of the number of force sensors, and (iv) a strapping distance for the mask and headgear based on outputs from the number of strap distance sensors. The method may further include the steps of (b) determining in the controller one or more of the following: (i) a lead change by comparing the determined total number of leads to prestored lead information, (ii) a strapping force change by comparing the determined strapping force to prestored strapping force information, (iii) a strapping force distribution change by comparing the determined strapping force distribution to prestored strapping force distribution information, and (iv) a strapping distance change by comparing the determined strapping distance to prestored strapping distance information. The method may further include the steps of (c) determining in the controller that the patient interface device change has occurred based on one or more of (i) the determined lead change, (ii) the determined strapping force change, (iii) the determined strapping force distribution change, and (iv) the determined strapping distance change.

The disclosed concept further includes a pressure support system that may comprise a mask, a headgear, and a controller. A number of force sensors and/or a number of strap distance sensors may be associated with the mask and the headgear. The controller may be structured and configured for (a) determining, while the mask and headgear are worn by the user and are coupled to the pressure support system during operation of the pressure support system, one or more of the following: (i) a total number of leads associated with the number of force sensors, (ii) a strapping force for the mask and headgear based on outputs from the number of force sensors, (iii) a strapping force distribution for the mask and headgear based on the outputs from at least one of the number of force sensors, and (iv) a strapping distance for the mask and headgear based on outputs from the number of strap distance sensors. Further, the controller may be structured and configured for (b) determining one or more of the following: (i) a lead change by comparing the determined total number of leads to prestored lead information, (ii) a strapping force change by comparing the determined strapping force to prestored strapping force information, (iii) a strapping force distribution change by comparing the determined strapping force distribution to prestored strapping force distribution information, and (iv) a strapping distance change by comparing the determined strapping distance to prestored strapping distance information. Further, the controller may be structured and configured for (c) determining a patient interface device change has occurred based on one or more of (i) the determined lead change, (ii) the determined strapping force change, (iii) the determined strapping force distribution change, and (iv) the determined strapping distance change.

Another aspect of the disclosed technology may further include a pressure support system that may comprise a blower for generating a flow of beathing gas. The pressure support system may further comprise a controller structured and configured for determining, while the mask and headgear are worn by the user and are coupled to the pressure support system during operation of the pressure support system, a number of strapping forces for the mask and headgear over time based on outputs from the number of force sensors. Further, the controller may be structured and configured for determining a rate of change of the number of strapping forces over time, and determining that the mask and headgear are worn out and should be replaced based on the rate of change.

BRIEF DESCRIPTION OF THE DRAWINGS

A full understanding of the invention can be gained from the following description of the preferred embodiments when read in conjunction with the accompanying drawings in which.

DETAILED DESCRIPTION OF THE INVENTION

Figure 1:
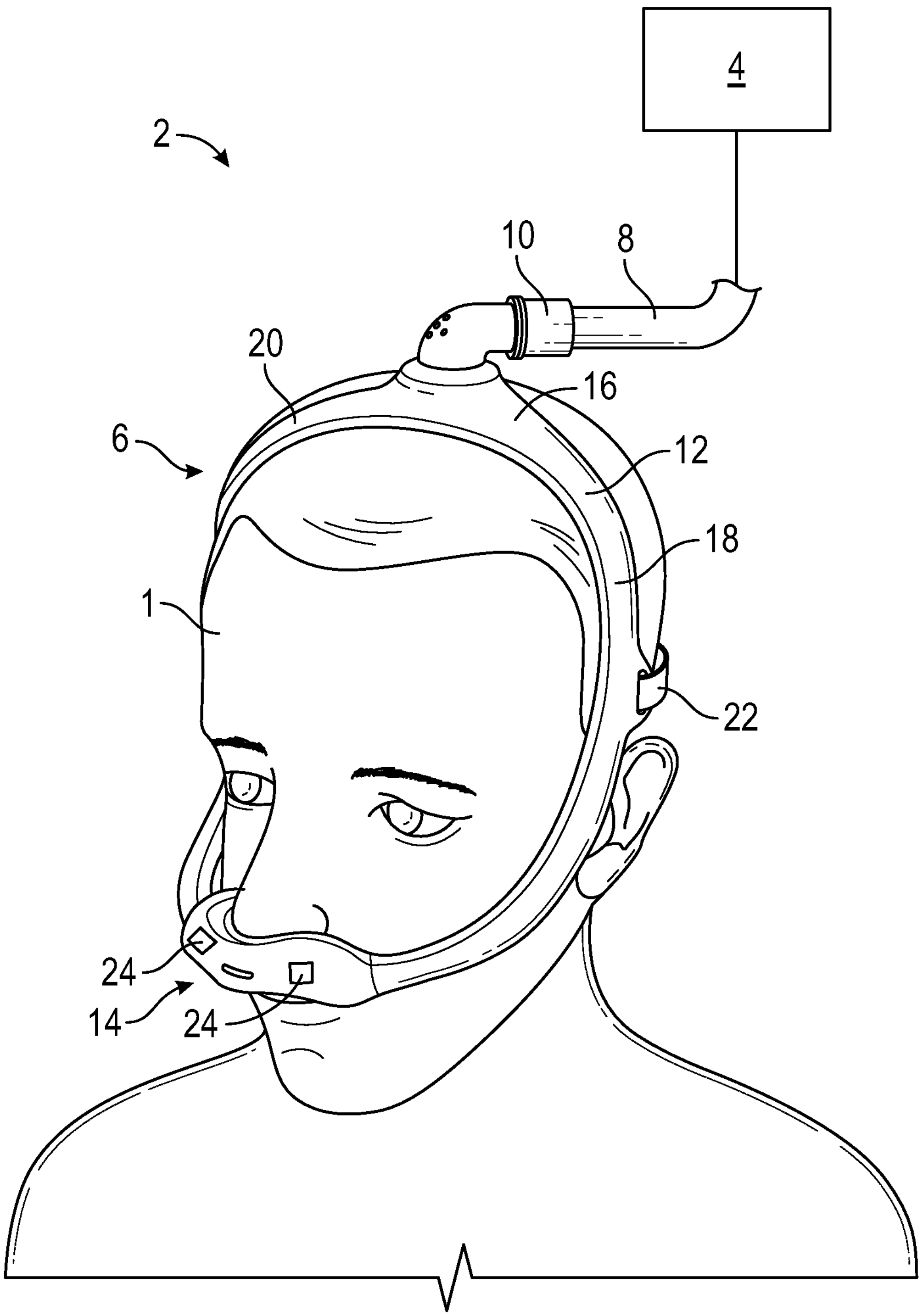
FIGS. 1 and 2 are schematic diagrams illustrating a system for identifying a patient interface device change in a pressure support system while the system is worn by a user according to an exemplary embodiment of the disclosed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The disclosed concept relates to systems and methods for identifying a patient interface device change in an airway pressure support system. More specifically, the disclosed concept provides, in the various embodiments described herein, an airway pressure support system in which changes in the connected patient interface device may be identified by the system based on the output of a number of sensors coupled to, or embedded in, the patient interface device. Example embodiments of the disclosed concept will be described with respect to patient interface device identification for the purposes of selecting or customizing respiratory therapy based on the identified patient interface device (e.g., a mask). However, it will be appreciated that the disclosed concept is also pertinent to other applications where patient interface device identification (ID) data is collected and potentially transmitted to other parties.

Figure 2:
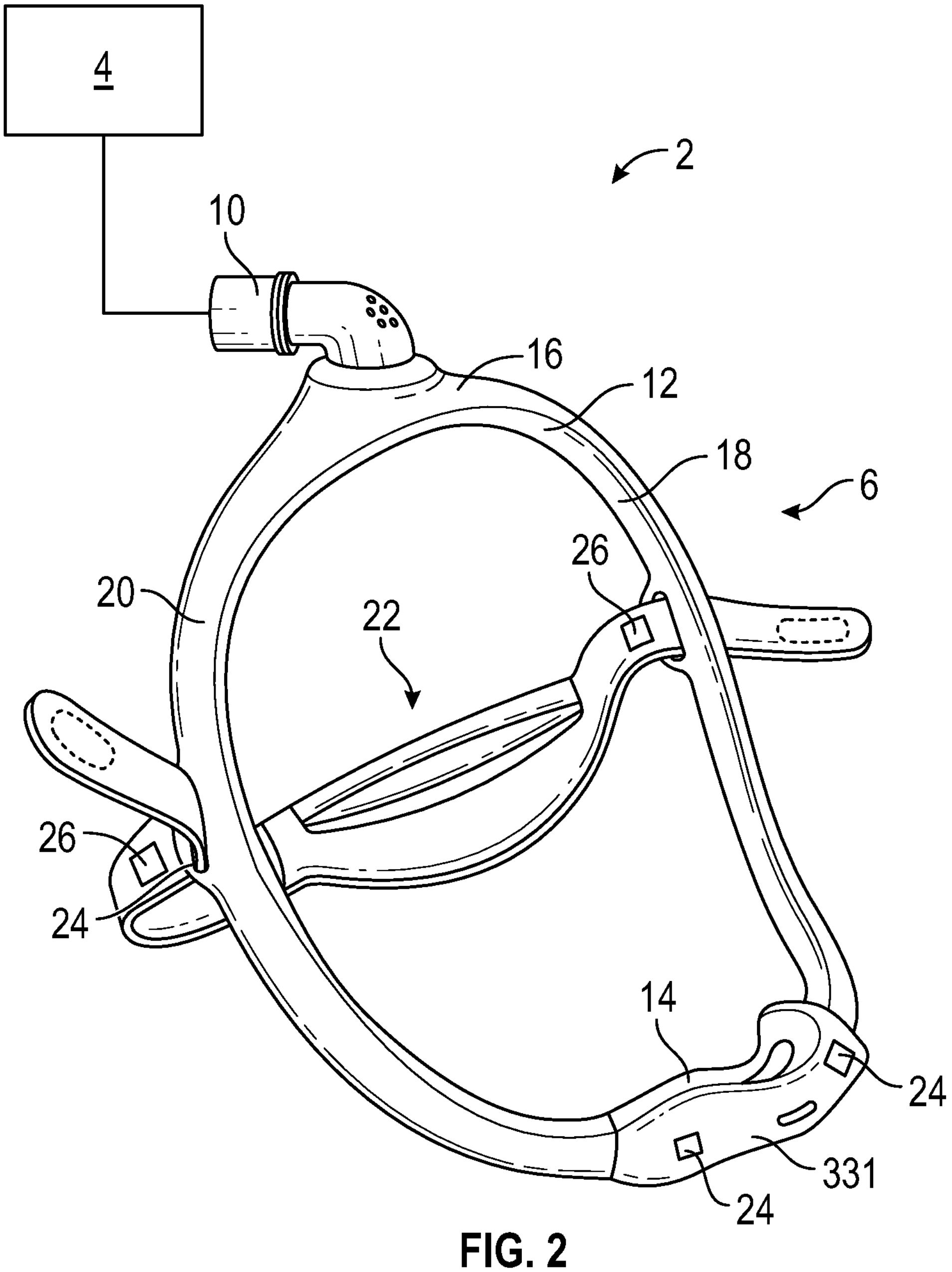
Figure 3:
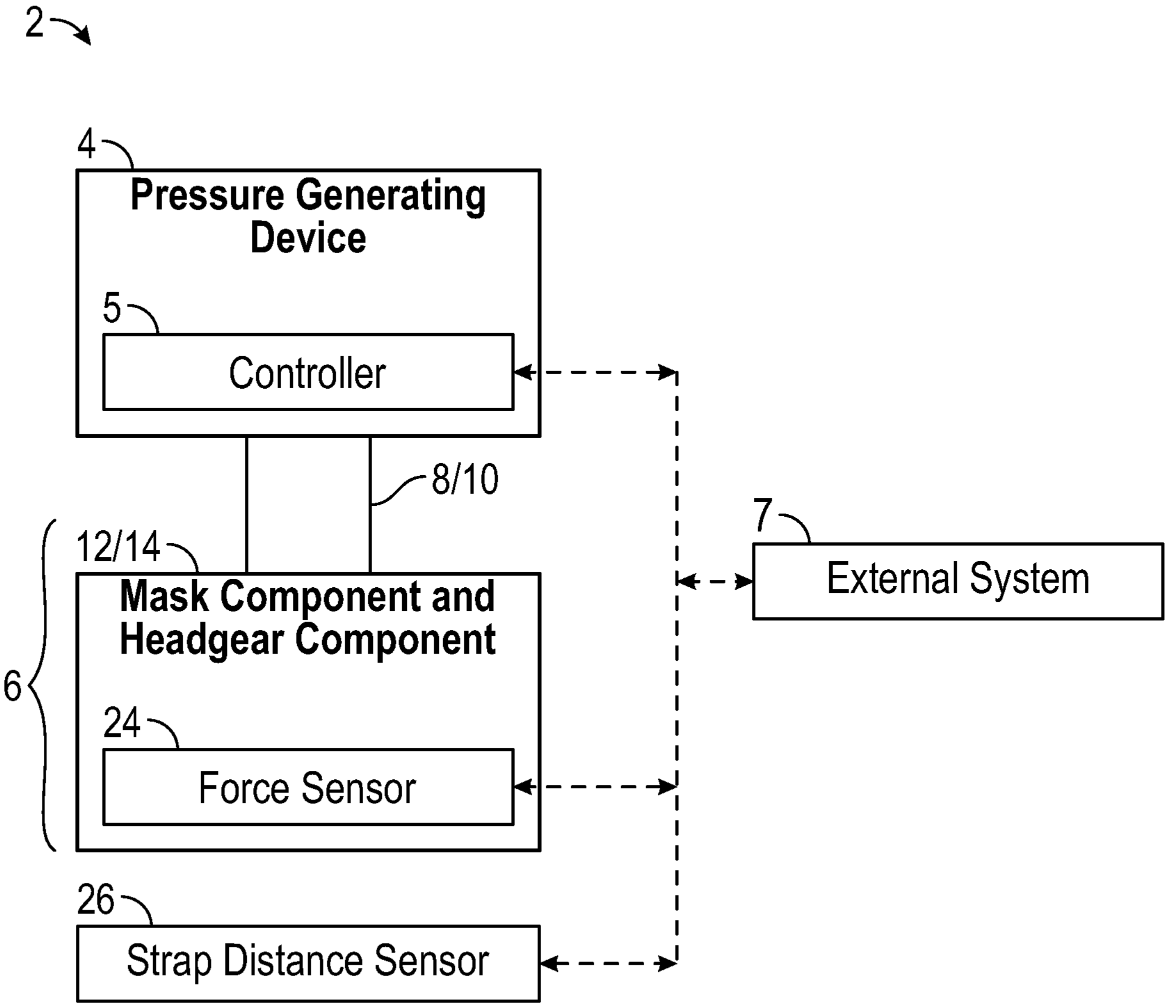
FIG. 3 is a block diagram of the system of FIGS. 1 and 2.

FIGS. 1 and 2 are schematic diagrams of a pressure support system 2 adapted to provide a regimen of respiratory therapy to a patient/user 1 according to one exemplary embodiment of the disclosed concept. In FIG. 1, pressure support system 2 is shown in a condition wherein it is coupled to the head of user 1, whereas FIG. 2 shows pressure support system 2 in a condition wherein it is not coupled to the head of user 1. FIG. 3 is a block diagram of pressure support system 2 of this embodiment.

Referring to FIGS. 1-3, system 2 includes a pressure generating device 4 (e.g., comprising a blower) that is structured to generate a flow of breathing gas, and a patient interface device 6 that is coupled to the pressure generating device 4 for delivering the flow of breathing gas to the airways of user 1. Pressure generating device 4 may include, without limitation, a ventilator, a constant pressure support device (such as a continuous positive airway pressure device, or CPAP device), a variable pressure device (e.g., BiPAP®, Bi-Flex®, or C-Flex™ devices manufactured and distributed by Respironics, Inc. of Murrysville, Pa.), or an auto-titration pressure support device.

As seen in FIGS. 1 and 2, patient interface device 6 includes a delivery conduit 8, a fluid coupling conduit 10 (e.g., in the form of an elbow connector as shown), a headgear component 12, and a mask component 14 (e.g., in the form of a nasal cushion as shown). The first end of delivery conduit 8 is coupled to the output of pressure generating device 4, and the second end of delivery conduit 8 is coupled to fluid coupling conduit 10. Headgear component 12 in the illustrated embodiment includes a frame portion 16 comprising a left conduit member 18 and a right conduit member 20, and a strap component 22 (including a number of straps) for securing headgear component 12 (and mask component 14 coupled thereto) to the head of user 1. As seen in FIGS. 1 and 2, fluid coupling conduit 10 is fluidly coupled to the top of frame portion 16 of headgear component 12. Mask component 14 is fluidly coupled to the distal end of each of left conduit 18 and right conduit 20. In the illustrated embodiment, mask component 14 is a nasal cushion made of a soft, flexible material, such as, without limitation, silicone, an appropriately soft thermoplastic elastomer, a closed-cell foam, or any other suitable material or combination of such materials. It is to be appreciated, however, that any type of mask component, such as a nasal/oral mask, a nasal pillow, or a full-face mask, which facilitates the delivery of the flow of breathing gas to the airway of a patient may be used as a sealing element while remaining within the scope of the present invention. Thus, as shown, patient interface device 6 provides a fluid path for delivery of the breathing gas from pressure generating device 4 to the airways of user 1 through delivery conduit 8, headgear component 12 and mask component 14.

In the exemplary embodiment, pressure generating device 4 includes a controller 5 for controlling operation of pressure support system 2 as described herein (FIG. 3). Controller 5 forming part of pressure generating device 4 may be, for example, a microprocessor, a microcontroller, or some other suitable processing device, which includes or is operatively coupled to a memory that provides a storage medium for data and software executable by controller 5 for controlling the operation of pressure generating device 4 and airway pressure support system 2.

Moreover, as seen in FIGS. 1 and 2, patient interface device 6 includes a number of force sensors, shown schematically in FIGS. 1 and 2 and labeled with reference number 24, for measuring a number of strapping forces for mask component 14 and/or headgear component 12 when patient interface device 6 is donned by user 1. Patient interface device 6 also includes a number of strap distance sensors, shown schematically in FIG. 2 and labeled with reference number 26, for measuring a current strapping distance/position of various elements of strap component 22 (e.g., where the straps are coupled to themselves or another part of headgear component 22 in the exemplary embodiment when patient interface device 6 is donned by user 1). The illustrated locations of force sensors 24 shown in FIGS. 1 and 2 are meant to be exemplary only, and it will be appreciated that such sensors may be located in alternative positions within the scope of the disclosure concept. For example, one or more force sensors 24 can be provided in the illustrated locations of straps distance sensors 26.

In the exemplary embodiment, force sensors 24 can be located at any location in patient interface device 6 as long as that location is under load (tension) when mask component 14 is adjusted (tightened). Distance sensors 26, on the other hand, would, in the exemplary embodiment, only be located where the adjustment happens (i.e., the straps themselves). Controller 5 described above is communicably coupled (using any suitable wired or wireless method) to number of force sensors 24 and number of strap distance sensors 26 in order to receive the signals generated by such sensors for use as described herein. In a non-limiting exemplary embodiment, the forces transmitted through mask component 14 and headgear component 12 are proportional to the air pressure delivered by pressure generation device 4 (i.e., the delivered air pressure acts to push the mask cushion off the face and this push is resisted by straps 22). Additionally, the magnitude of these forces exerted onto straps 22 by the delivered air pressure depends on the size and shape of the mask cushion. Accordingly, system 2 may further include at least one air pressure sensor coupled to patient interface device 6. Accordingly, controller 5 is able to identify patient interface device 6 based on the sensor measurements relative to the delivered air pressure.

Figure 4:
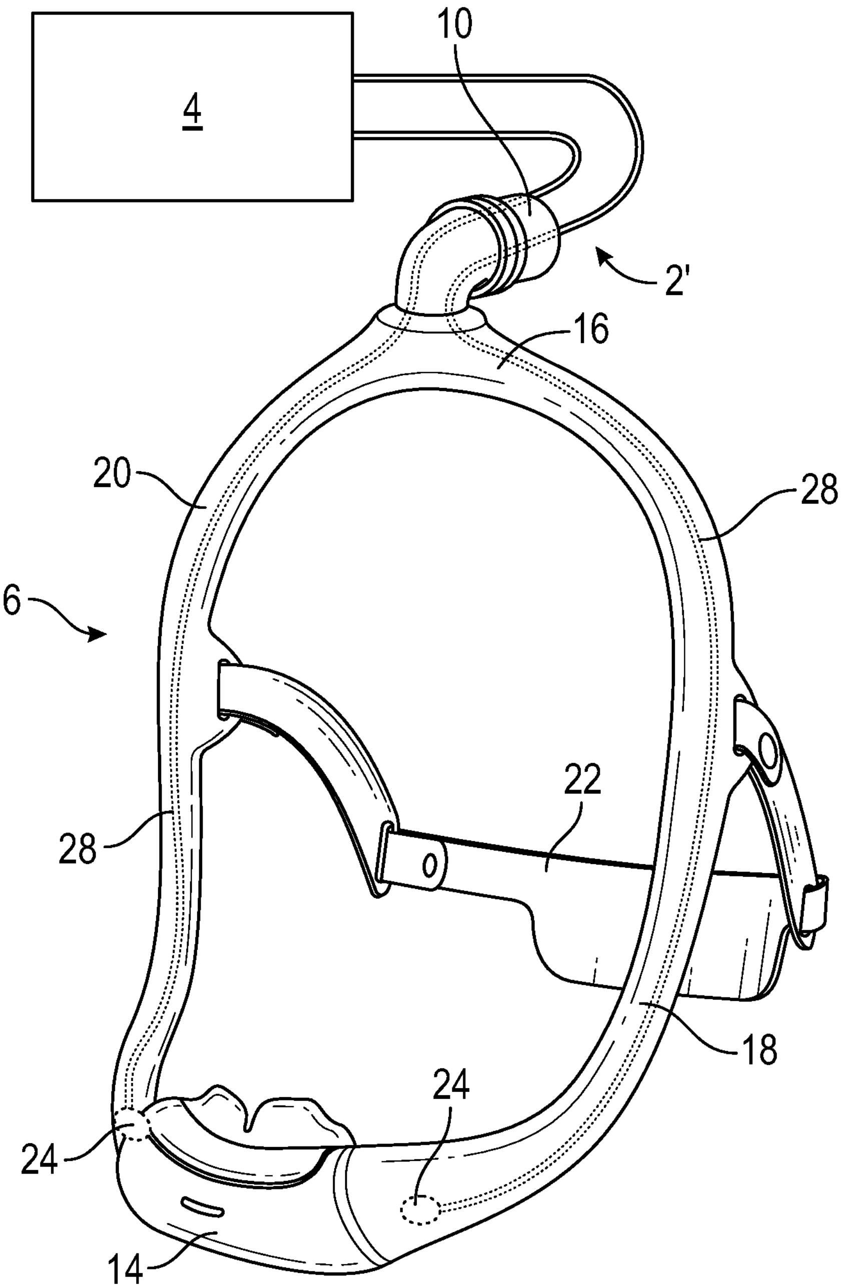
FIG. 4 is a schematic diagram illustrating a system for identifying a patient interface device change in a pressure support system with a pair of force sensors and force sensor leads according to an exemplary embodiment of the disclosed concept.
Figure 5:
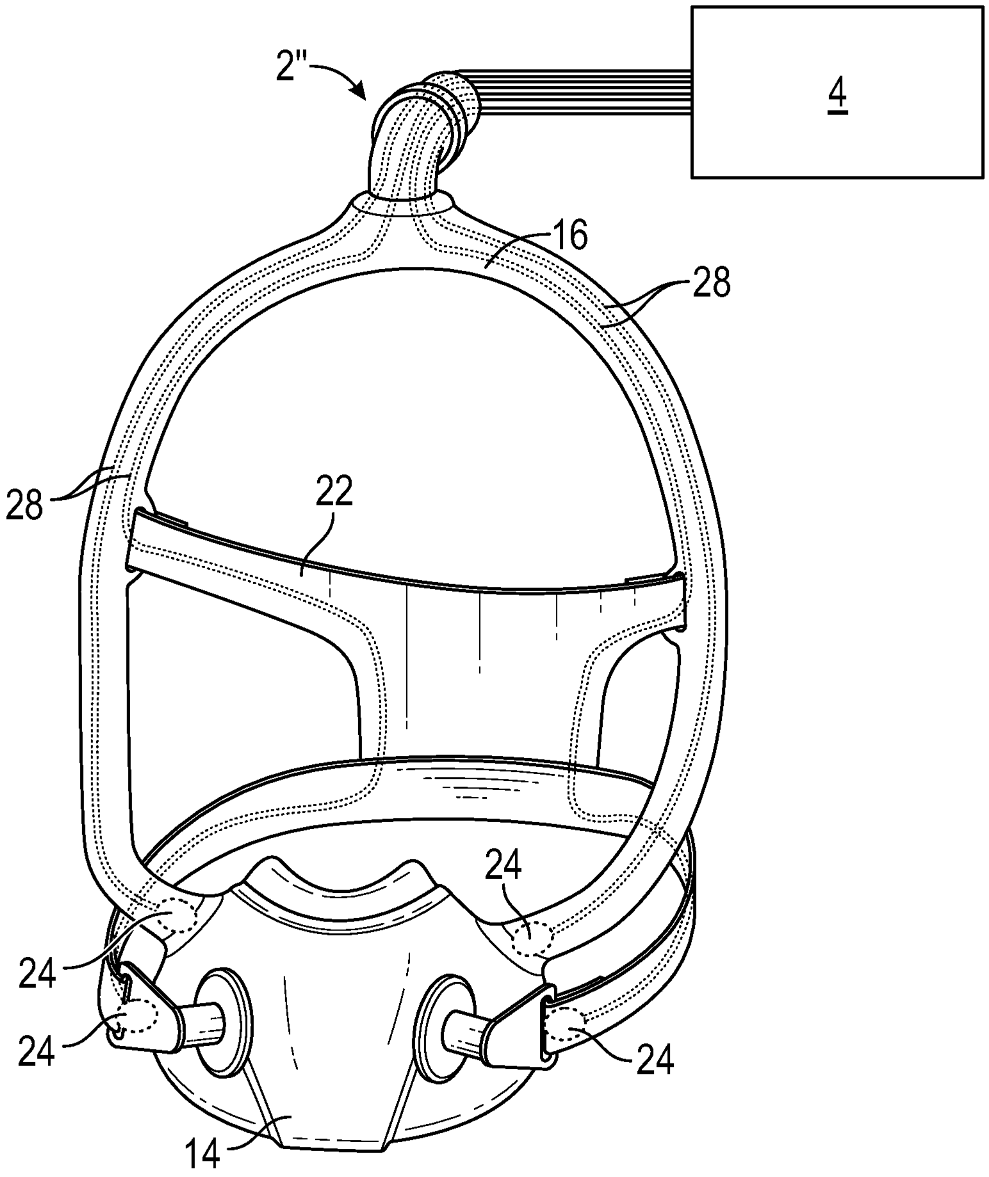
FIG. 5 is a schematic diagram illustrating a system for identifying a patient interface device change in a pressure support system with a number of force sensors and force sensor leads according to another exemplary embodiment of the disclosed concept.

FIG. 4 is a schematic diagram of a pressure support system 2' according to one particular exemplary embodiment wherein number of force sensors 24 is coupled to controller 5 by way of a number of leads 28. In particular, referring to FIG. 4, pressure support system 2' is similar to pressure support system 2, and like parts are labeled with like reference numbers. As seen in FIG. 4, each force sensor 24 is coupled to controller 5 of pressure generating device 4 by way of an associated lead 28 that is coupled to frame member 16 of headgear component 12. FIG. 5 is a schematic diagram of a pressure support system 2" according to another particular exemplary embodiment wherein number of force sensors 24 is coupled to controller 5 by way of a number of leads 28. In particular, pressure support system 2" is similar to pressure support system 2', and like parts are labeled with like reference numbers. However, pressure support system 2" includes a mask component 14 in the form of a full-face mask, as opposed to the nasal cushion shown in the FIG. 4 embodiment. It will be understood that FIGS. 4 and 5 are exemplary only, and that other configurations for coupling the various sensors to controller 5 are contemplated within the scope of the disclosed concept. In these exemplary embodiments, controller 5 detects the number of (active) leads (or incoming signals) (via a wired or wireless connection) and identifies the mask type (or any kind of defined sub-group) via a lookup table linking no of leads to mask (sub-)types.

In a non-limiting exemplary embodiment, at least one force sensor 24 is integrated into the connection between at least one of the straps of strap component 22 and the corresponding load bearing portion of mask component 14. In a further non-limiting embodiment, each of the number of load bearing portions of mask component 14 has a corresponding force sensor 24 integrated therein. In a further non-limiting embodiment, each of the number of straps of strap component 22 has a corresponding force sensor 24 integrated therein. Accordingly, in such embodiments, each of number of force sensors 24 may be disposed to determine the amount of stress or strain on mask component 14 and/or headgear component 12 when worn by user 1. It is to be understood that number of force sensors 24 may be distributed throughout mask component 14, headgear component 12, and strap component 22 so that controller 5 is able to measure all internal and external forces to which patient interface device 6 is subjected.

In another non-limiting exemplary embodiment, each of number of strap distance sensors 26 may be a sensor array disposed to identify the length of a corresponding strap of strap component 22 that is pulled through the corresponding load bearing portion. In another non-limiting exemplary embodiment, each of number of strap distance sensors 26 may be a sensor array used to identify a length of the corresponding portion of strap component 22 that remains to be pulled through the corresponding load bearing portion. Further, embodiments of number of force sensors 24 and number of strap distance sensors 26 may include one or more of the following: magnetometers, strain sensors, resistive sensors, capacitive sensors, pressure sensors, optical sensors, radio frequency identification (RFID) transceivers, and proximity sensors. In a further non-limiting embodiment, mask component 14, headgear component 12, and strap component 22 are each equipped with a dedicated set of sensors (e.g., number of force sensors 24 and number of distance sensors 26) that are communicably coupled to controller 5 of pressure generating device 4. Accordingly, controller 5 is able to identify and monitor the various components of patient interface device 6 even when these components are integrated into, or comingled with, third-party mask systems.

Figure 6:
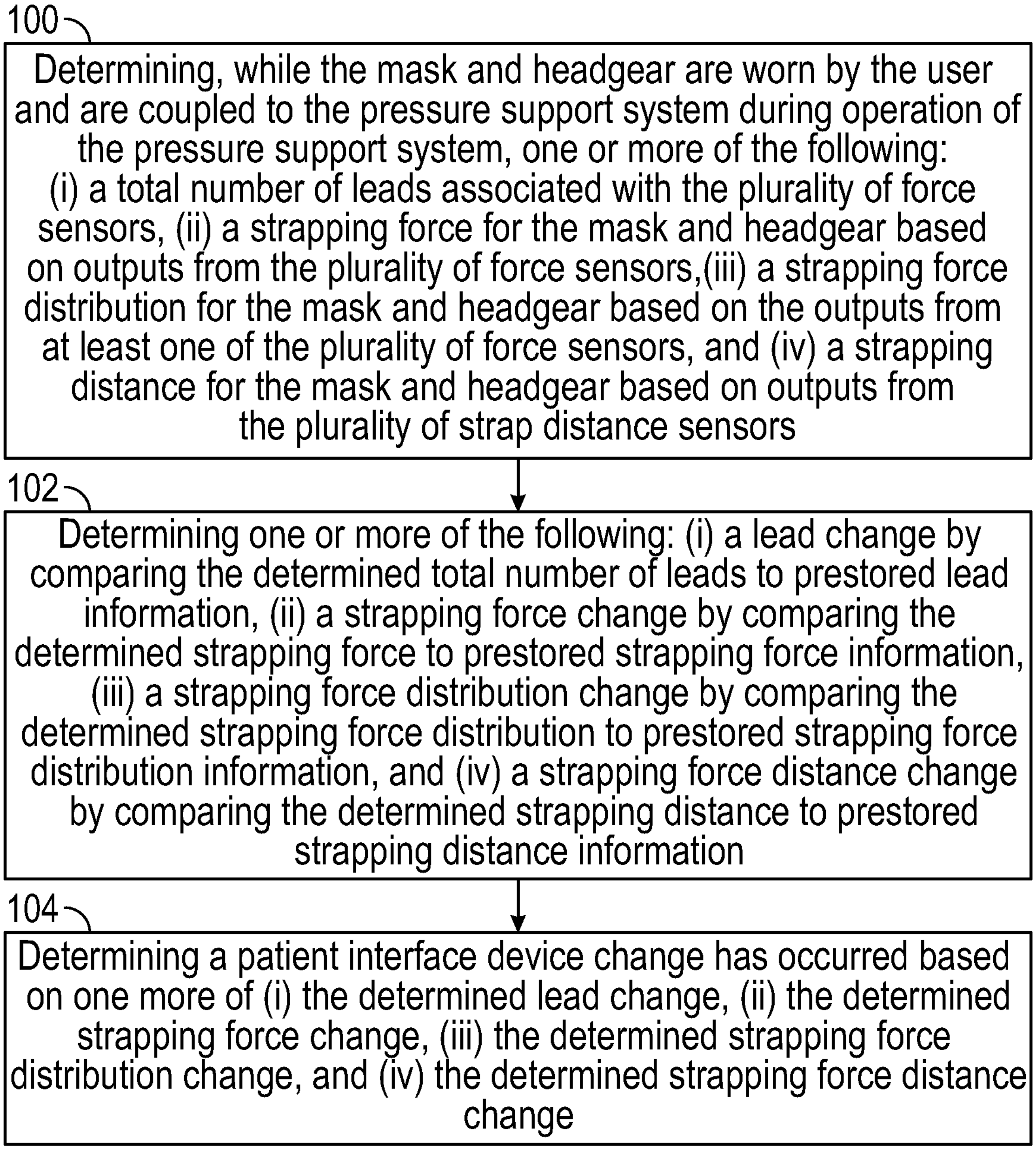
FIG. 6 is a flowchart illustrating the overall method according to an exemplary embodiment of the disclosed concept.

FIG. 6 is a flowchart showing a method of identifying a patient interface device change in a pressure support system according to an exemplary embodiment of the disclosed concept. For illustrative purposes, the method will be described in connection with the pressure support system embodiments 2, 2', and 2" discussed above, although it will be understood that this is meant to be exemplary only. In addition, in the exemplary embodiment, the method of FIG. 6 is implemented in one or more software routines that are stored and executed by controller 5 forming part of pressure generating device 4.

Referring to FIG. 6, the method of the disclosed concept begins at step 100 by determining, in controller 5, while mask component 14 and headgear component 12 are worn by user 1 and are coupled to pressure support system 2 during operation of pressure support system 2, one or more of the following: (i) a total number of leads 28 or otherwise incoming signals associated with number of force sensors 24, (ii) a strapping force for mask component 14 and headgear component 12 based on outputs from number of force sensors 24, (iii) a strapping force distribution for mask component 14 and headgear component 12 based on the outputs from at least one of number of force sensors 24, and (iv) a strapping distance for mask component 14 and headgear component 12 based on outputs from number of strap distance sensors 26.

The total number of leads 28 may refer to the number of sensor probe leads 28 that are integrated into patient interface device 6 as shown in FIGS. 4 and 5. In a non-limiting embodiment, the total number of leads 28 may refer to the number of data generating components that are communicably coupled to controller 5. The strapping force may refer to the amount of physical strain exerted on patient interface device 6, including the number of load bearing portions of mask component 14 as measured by number of force sensors 24. The strapping force distribution may refer to a virtual model that may represent the output from one or more of number of force sensors 24 at once. The strapping distance may refer to a measurement of the length of the corresponding strap from strap component 22 that is pulled through the corresponding load bearing portion of mask component 14 (FIG. 2).

The method continues at step 102 by determining, in controller 5, one or more of the following: (i) a lead change by comparing the determined total number of leads 28 to prestored lead information, (ii) a strapping force change by comparing the determined strapping force to prestored strapping force information, (iii) a strapping force distribution change by comparing the determined strapping force distribution to prestored strapping force distribution information, and (iv) a strapping distance change by comparing the determined strapping distance to prestored strapping distance information. This determining enables controller 5 to assess if there is any variance between the current measured parameters and certain prestored parameter values. The prestored lead information, the prestored strapping force information, the prestored strapping force distribution information, and the prestored strapping distance information may be stored on controller 5 locally or provided by an external system 7 (FIG. 3). Accordingly, controller 5 may analyze one or more relevant changes when assessing patient interface device 6. The criteria for determining relevant changes may be set by controller 5 or by external system 7.

The method continues at step 104 by determining, in controller 5, that a patient interface device change has in fact occurred based on one or more of (i) the determined lead change, (ii) the determined strapping force change, (iii) the determined strapping force distribution change, and (iv) the determined strapping distance change. This determining enables controller 5 to assess whether the current measured parameters are sufficiently different from the prestored parameters to signify a change in patient interface device 6 that is currently being used. The criteria for determining relevant determined changes may be set by controller 5 or by external system 7. In one embodiment, controller 5 is able to determine whether a patient interface device change has occurred based on the determined strapping force change being larger than a first threshold, the determined strapping force distribution change being larger than a second threshold, or the determined strapping distance change being larger than a third threshold. The first threshold, the second threshold, and the third threshold may refer to acceptable error bands that serve as criteria for assessing whether or not the determined strapping force change, the determined strapping force distribution change, and the determined strapping distance change signify a patient interface device change.

Embodiments of the disclosed concept may execute a number of additional processes when performing steps 100 and 102. As described hereinabove, controller 5 may analyze one or more relevant data streams, operational parameters, and determined changes when assessing if patient interface device 6 has been changed. For example, in one embodiment, step 100 may comprise determining at least the total number of leads 28 and step 102 may comprise determining at least the lead change. The total number of leads 28 refers to sensor probe leads 28 associated with number of force sensors 24 actively measuring strapping forces and communicating with controller 5, as identified during step 100. During step 102, controller 5 may compare the total number of leads 28 to prestored references (e.g., a look-up table that correlates the total number of leads 28 to one or more mask types or subtypes) that include the number of active leads 28 associated with one or more mask types. Accordingly, controller 5 executes the appropriate process once the patient interface device change is determined during step 104.

In another embodiment, step 100 may comprise determining at least the strapping force, and step 102 may comprise determining at least the strapping force change. In still another embodiment, step 100 may comprise determining at least the strapping force distribution, and step 102 may comprise determining at least the strapping force distribution change. In another embodiment step 100 may comprise determining at least the strapping distance, and step 102 may comprise determining at least the strapping distance change. In yet another embodiment, step 100 may comprise determining two or more of the total number of leads 28, the strapping force, the strapping force distribution, and the strapping distance, and step 102 may comprise determining two or more of the lead change the strapping force change, the strapping force distribution change, and the strapping distance change.

In an additional embodiment, step 100 may comprise determining three or more of the total number of leads 28, the strapping force, the strapping force distribution, and the strapping distance, and step 102 may comprise determining three or more of the lead change the strapping force change, the strapping force distribution change, and the strapping distance change. In yet an additional embodiment, step 100 may comprise determining all of the total number of leads 28, the strapping force, the strapping force distribution, and the strapping distance, and step 102 may comprise determining all of the lead change the strapping force change, the strapping force distribution change, and the strapping distance change.

Figure 7:
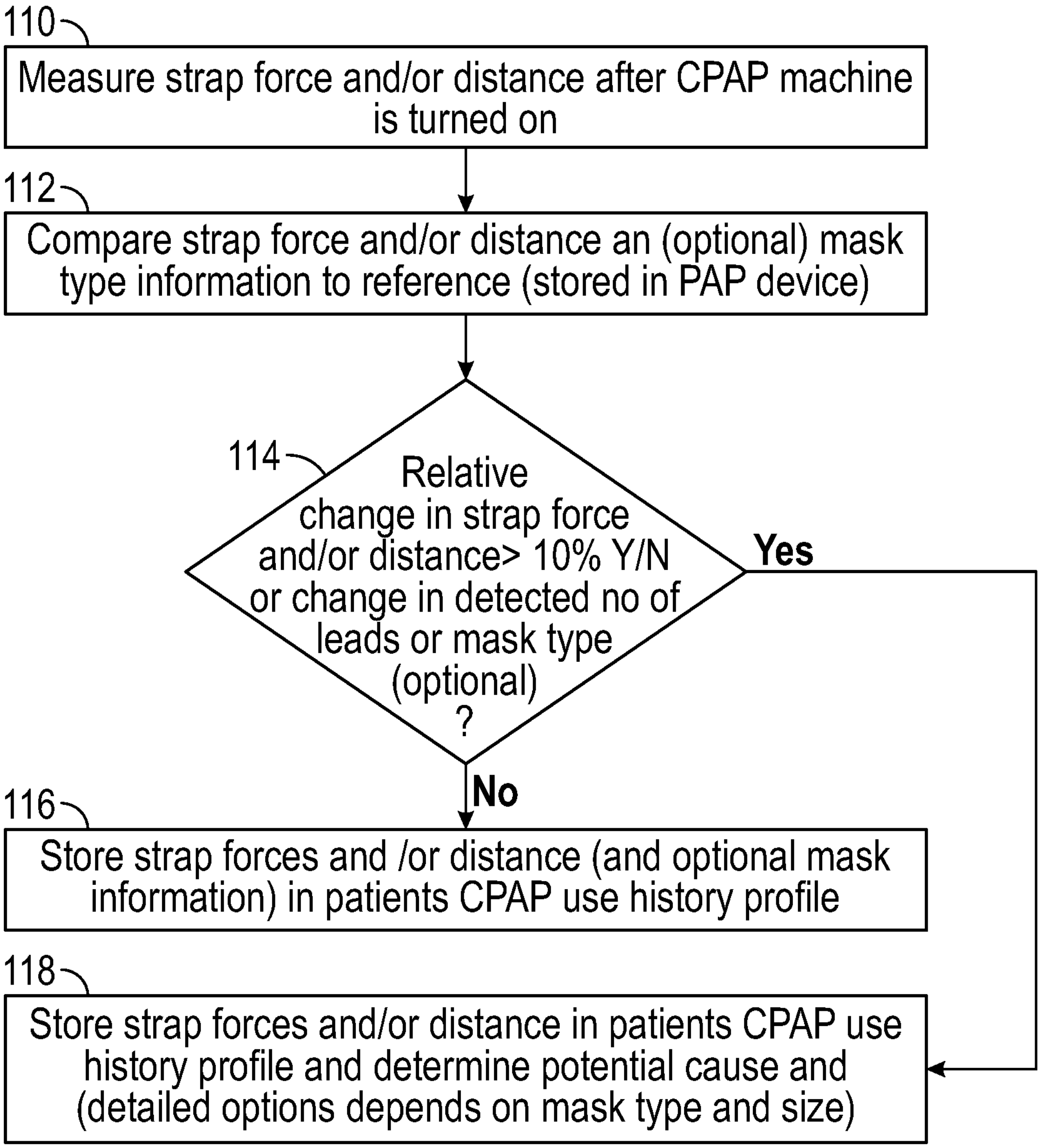
FIG. 7 is a flowchart illustrating one particular implementation of the method of FIG. 6 according to a non-limiting exemplary embodiment of the disclosed concept.

FIG. 7 is a flowchart of one particular implementation of the method of FIG. 6 according to a non-limiting exemplary embodiment of the disclosed concept. This implementation begins at step 110 by measuring with number of force sensors 24 and number of strap distance sensors 26 at least one of the strap force and the strap distance for patient interface 6 device after pressure generating device 4 is turned on. The method continues at step 112 by comparing at least one of the measured strap force and the measured strap distance to stored references with controller 5. The method continues at step 114 with controller 5 determining if the relative change in at least one of the measured strap force and the measured strap distance is greater than 10%; and if the number of leads 28 has changed based on the output from number of force sensors 24. If any of the above criteria are met the method proceeds to step 118 by storing at least one of the measured strap force and the measured strap distance in the patient profile and then determining the potential cause for the measured relative change. The relative change is determined by the comparisons between the measured strap force, the measured strap distance, and the stored references. The options for assessing the potential cause may vary depending on mask type. If the above-reverenced criteria are not met, the method proceeds to step 116 by storing at least one of the measured strap force and the measured strap distance in the patient profile. Controller 5 may incorporate information relating to mask type into steps 112-118.

Figure 8:
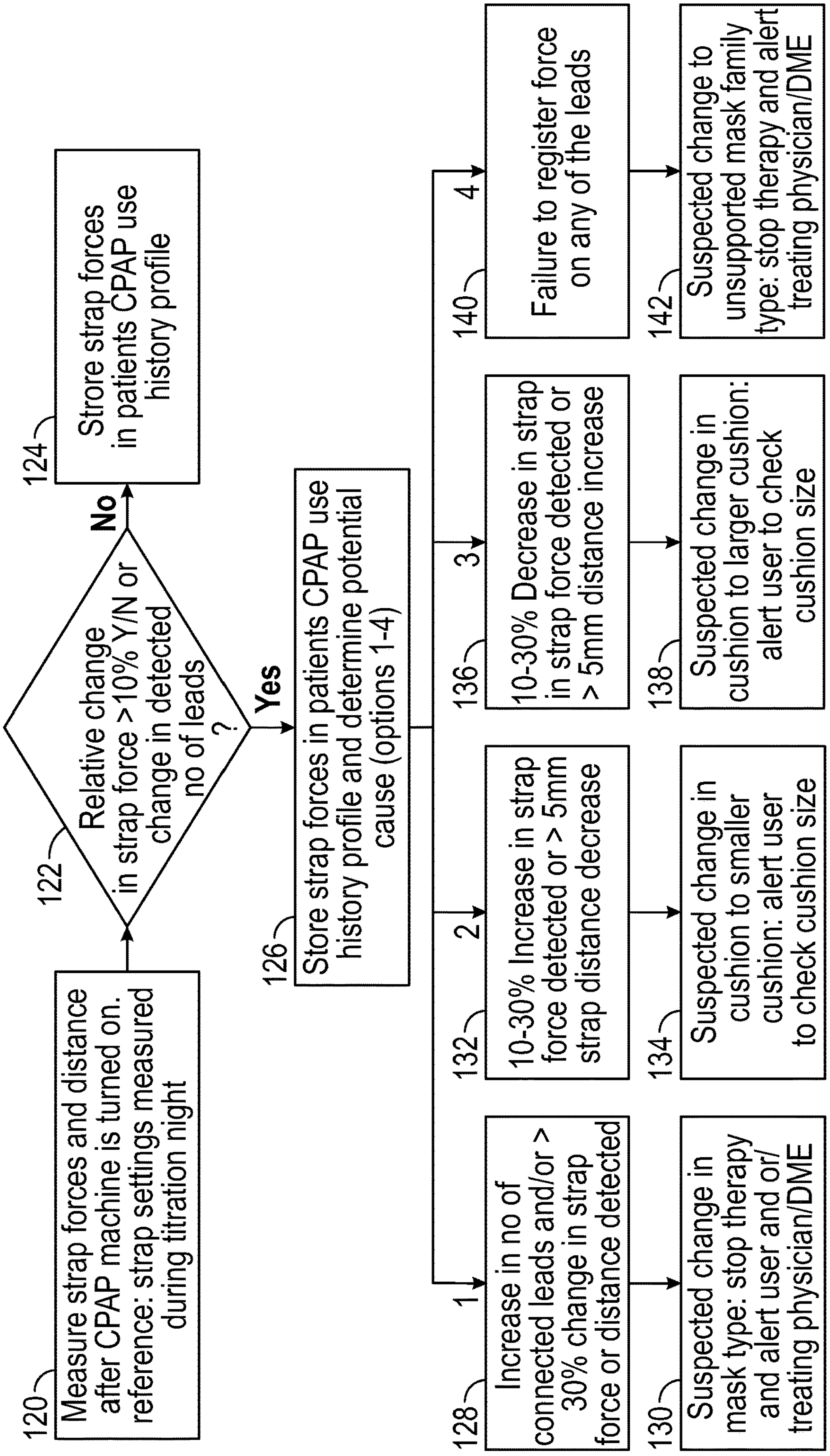
FIG. 8 is a flowchart illustrating another particular implementation of the method of FIG. 6 according to an alternative non-limiting exemplary embodiment of the disclosed concept.

FIG. 8 is a flowchart of another particular implementation of the method of FIG. 6 according to another non-limiting exemplary embodiment of the disclosed concept. This implementation is a continuation of FIG. 7 and steps 120-126 are analogous to steps 110-118. However, the output from number of force sensors 24 and number of strap distance sensors 26 is measured against reference values that were acquired during a titration night. The continuation begins at step 126 with controller 5 executing a number of optional subprocesses. For option 1, the method continues at step 128 with controller 5 determining whether at least one of the following has occurred an increase in the number of connected leads 28 and a greater than 30% change in the measured strap distance. If either criterion is met, the method continues at step 130 with controller 5 determining that a mask change is suspected, stopping the therapy, and alerting at least one of user 1 and the user's treating physician. For option 2, the method continues at step 132 with controller 5 determining if there is a 10-30% increase in the measured strap force or if there is a greater than 5 mm decrease in strap distance. If one of these criteria is met, the method continues at step 134 with controller 5 determining that a mask change to a mask 6 with a smaller cushion is suspected and alerting at least one of user 1 and the user's treating physician to check the size of the cushion. For option 3, the method continues at step 136 with controller 5 determining if there is a 10-30% decrease in the measured strap force or if there is a greater than 5 mm increase in strap distance. If one of these criteria is met, the method continues at step 138 with controller 5 determining that a mask change to a mask 6 with a larger cushion is suspected and alerting at least one of user 1 and the user's treating physician or other relevant caregiver to check the size of the cushion. For option 4, the method continues at step 140 with controller 5 determining if there is no force measured on any of leads 28 or force sensors 24.

The method continues at step 142 with controller 5 determining that a mask change to an unsupported mask type is suspected, stopping the therapy, and alerting at least one of user 1 and the user's treating physician. In a non-limiting exemplary embodiment, controller 5 may execute any number of patient interaction processes including, but not limited to, prompting to change therapy settings to higher or lower pressure depending on the mask type and size, prompting to purchase a better fitting mask, and coupling a control mechanism to patient interface device 6 that auto adjusts therapy pressure depending on mask type and size.

Figure 9:
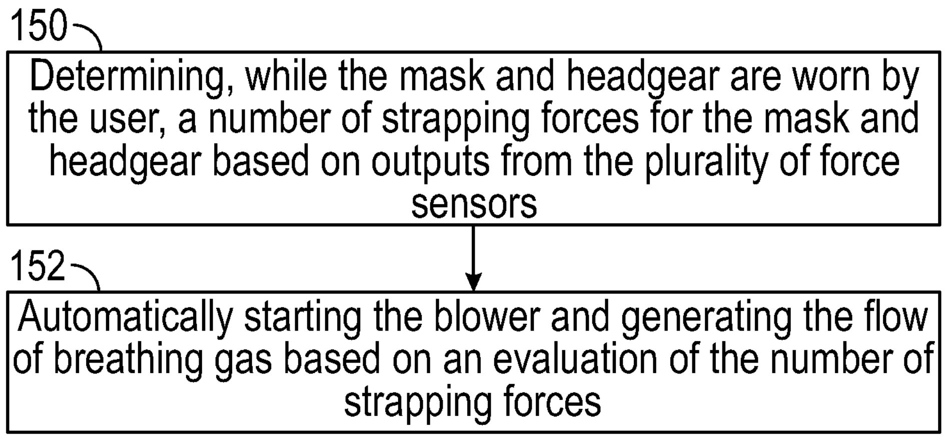
FIG. 9 is a flowchart of a method of using mask sensor data to automatically start the pressure generating device according to an exemplary embodiment of the disclosed concept.

FIG. 9 is a flowchart of a method of automatically starting pressure support system embodiments 2, 2' and 2" discussed above according to another non-limiting exemplary embodiment of the disclosed concept. The method begins at step 150 by having controller 5 determine, while mask component 14 and headgear component 12 are worn by user 1, a number of strapping forces for mask component 14 and headgear component 12 based on outputs from number of force sensors 24. The method continues at step 152 by having controller 5 automatically start blower 4 and generating the flow of breathing gas based on an evaluation of the number of strapping forces. Accordingly, controller 5 may be structured and configured for modifying characteristics of the flow of breathing gas based on the number of strapping forces.

Figure 10:
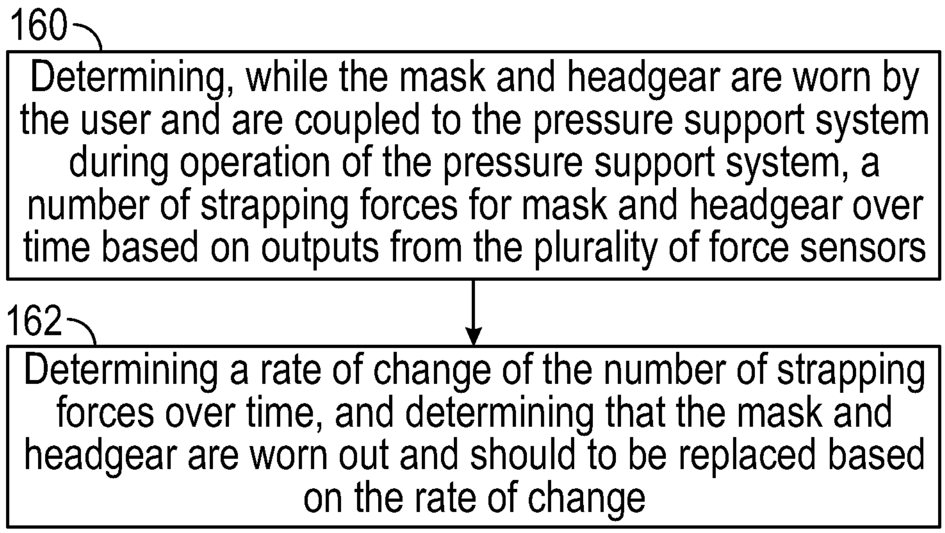
FIG. 10 is a flowchart of a method of using mask sensor data to automatically determine an amount of wear according to an exemplary embodiment of the disclosed concept.

FIG. 10 is a flowchart of a method of automatically determining whether mask component 14 and/or headgear component 12 of pressure support system embodiments 2, 2', and 2" discussed above are worn out and need to be replaced according to another non-limiting exemplary embodiment of the disclosed concept. The method begins at step 160 by having controller 5 determine, while mask 6 and headgear 12 are worn by user 1 and are coupled to pressure support system 4 during operation of pressure support system 4, a number of strapping forces for mask component 14 and headgear component 12 over time based on outputs from number of force sensors 24. Accordingly, controller 5 may keep and analyze longitudinal records of the operational parameters of patient interface device 6. The method continues at 162 by having controller 5 determine a rate of change of the number of strapping forces over time, and determining that mask component 14 and headgear component 12 are worn out and should be replaced based on the rate of change. The rate of change of the number of strapping forces may decrease, for example, if the elasticity of strap component 22 has decreased due to age or usage. Further, the rate of change may change if a sensor (24 or 26) or probe lead 28 is disconnected or damaged.

It is contemplated that aspects of the disclosed concept can be embodied as computer readable codes on a tangible computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage devices.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of disclosed concept which is to be given the full breadth of the claims appended and any and all equivalents thereof.

What is claimed is:

1. A method of identifying a patient interface device change in a pressure support system having a controller based on a mask and a headgear worn by a user, wherein a number of force sensors and/or a number of strap distance sensors are associated with the mask and the headgear, the method comprising:

(a) determining in the controller, while the mask and headgear are worn by the user, one or more of the following: (i) a total number of leads associated with the number of force sensors, (ii) a strapping force for the mask and headgear based on outputs from the number of force sensors, (iii) a strapping force distribution for the mask and headgear based on the outputs from at least one of the number of force sensors, and (iv) a strapping distance for the mask and headgear based on outputs from the number of strap distance sensors;

(b) determining in the controller one or more of the following: (i) a lead change by comparing the determined total number of leads to prestored lead information, (ii) a strapping force change by comparing the determined strapping force to prestored strapping force information, (iii) a strapping force distribution change by comparing the determined strapping force distribution to prestored strapping force distribution information, and (iv) a strapping distance change by comparing the determined strapping distance to prestored strapping distance information; and (c) determining in the controller that the patient interface device change has occurred based on one or more of (i) the determined lead change, (ii) the determined strapping force change, (iii) the determined strapping force distribution change, and (iv) the determined strapping distance change.

2. The method according to claim 1, wherein the determining in the controller that the patient interface device change has occurred is based on the determined strapping force change being larger than a first threshold, the determined strapping force distribution change being larger than a second threshold, or the determined strapping distance change being larger than a third threshold.

3. The method according to claim 1, wherein (a) comprises determining at least the total number of leads, and wherein (b) comprises determining at least the lead change.

4. The method according to claim 1, wherein (a) comprises determining at least the strapping force, and wherein (b) comprises determining at least the strapping force change.

5. The method according to claim 1, wherein (a) comprises determining at least the strapping force distribution, and wherein (b) comprises determining at least the strapping force distribution change.

6. The method according to claim 1, wherein (a) comprises determining at least the strapping distance, and wherein (b) comprises determining at least the strapping distance change.

7. The method according to claim 1, wherein (a) comprises determining two or more of the total number of leads, the strapping force, the strapping force distribution, and the strapping distance, and wherein (b) comprises determining two or more of the lead change the strapping force change, the strapping force distribution change, and the strapping distance change.

8. The method according to claim 1, wherein (a) comprises determining three or more of the total number of leads, the strapping force, the strapping force distribution, and the strapping distance, and wherein (b) comprises determining three or more of the lead change the strapping force change, the strapping force distribution change, and the strapping distance change.

9. The method according to claim 1, wherein (a) comprises determining all of the total number of leads, the strapping force, the strapping force distribution, and the strapping distance, and wherein (b) comprises determining all of the lead change the strapping force change, the strapping force distribution change, and the strapping distance change.

10. The method according to claim 1, wherein each of the one or more of the determined strapping force change, the determined strapping force distribution change, and the determined strapping distance change is also determined based on a level of pressure being delivered to the user while the mask and headgear are worn by the user.

11. A pressure support system, comprising:

a mask and a headgear, wherein a number of force sensors and/or a number of strap distance sensors are associated with the mask and the headgear; and a controller structured and configured for:

(a) determining, while the mask and headgear are worn by a user, one or more of the following: (i) a total number of leads associated with the number of force sensors, (ii) a strapping force for the mask and headgear based on outputs from the number of force sensors, (iii) a strapping force distribution for the mask and headgear based on the outputs from at least one of the number of force sensors, and (iv) a strapping distance for the mask and headgear based on outputs from the number of strap distance sensors;

(b) determining one or more of the following: (i) a lead change by comparing the determined total number of leads to prestored lead information, (ii) a strapping force change by comparing the determined strapping force to prestored strapping force information, (iii) a strapping force distribution change by comparing the determined strapping force distribution to prestored strapping force distribution information, and (iv) a strapping distance change by comparing the determined strapping distance to prestored strapping distance information; and (c) determining a patient interface device change has occurred based on one or more of (i) the determined lead change, (ii) the determined strapping force change, (iii) the determined strapping force distribution change, and (iv) the determined strapping distance change.

12. The pressure support system according to claim 11, wherein the determining that the patient interface device change has occurred is based on the determined strapping force change being larger than a first threshold, the determined strapping force distribution change being larger than a second threshold, or the determined strapping distance change being larger than a third threshold.

13. The pressure support system according to claim 11, wherein (a) comprises determining at least the total number of leads, and wherein (b) comprises determining at least the lead change.

14. The pressure support system according to claim 11, wherein (a) comprises determining at least the strapping force, and wherein (b) comprises determining at least the strapping force change.

15. The pressure support system according to claim 11, wherein (a) comprises determining at least the strapping force distribution, and wherein (b) comprises determining at least the strapping force distribution change.

16. The pressure support system according to claim 11, wherein (a) comprises determining at least the strapping distance, and wherein (b) comprises determining at least the strapping distance change.

17. The pressure support system according to claim 11, wherein (a) comprises determining two or more of the total number of leads, the strapping force, the strapping force distribution, and the strapping distance, and wherein (b) comprises determining two or more of the lead change the strapping force change, the strapping force distribution change, and the strapping distance change.

18. The pressure support system according to claim 11, wherein (a) comprises determining three or more of the total number of leads, the strapping force, the strapping force distribution, and the strapping distance, and wherein (b) comprises determining three or more of the lead change the strapping force change, the strapping force distribution change, and the strapping distance change.

19. The pressure support system according to claim 11 wherein (a) comprises determining all of the total number of leads, the strapping force, the strapping force distribution, and the strapping distance, and wherein (b) comprises determining all of the lead change the strapping force change, the strapping force distribution change, and the strapping distance change.

20. The system according to claim 11, wherein each of the one or more of the determined strapping force change, the determined strapping force distribution change, and the determined strapping distance change is also determined based on a level of pressure being delivered to the user while the mask and headgear are worn by the user.

21. A pressure support system, comprising:

a blower for generating a flow of beathing gas;

a mask and a headgear, wherein a number of force sensors is associated with the mask and the headgear; and a controller structured and configured for:

determining, while the mask and headgear are worn by a user, a number of strapping forces for the mask and headgear based on outputs from the number of force sensors, automatically starting the blower and generating the flow of breathing gas based on an evaluation of the number of strapping forces.

22. A pressure support system, comprising:

a blower for generating a flow of beathing gas;

a mask and a headgear, wherein a number of force sensors is associated with the mask and the headgear; and a controller structured and configured for:

determining, while the mask and headgear are worn by a user and are coupled to the pressure support system during operation of the pressure support system, a number of strapping forces for the mask and headgear over time based on outputs from the number of force sensors, determining a rate of change of the number of strapping forces over time, and determining that the mask and headgear are worn out and should be replaced based on the rate of change.

* * * * *